(12) United States Patent
Linares et al.

(10) Patent No.: US 7,404,791 B2
(45) Date of Patent: Jul. 29, 2008

(54) DEVICE FOR RADIATION TREATMENT OF PROLIFERATIVE TISSUE SURROUNDING A CAVITY IN AN ANIMAL BODY

(75) Inventors: Luis A. Linares, Metairie, LA (US); Johann Kindlein, Oberhausen (DE)

(73) Assignee: Nucletron B.V., Veenendaal (NL)

( * ) Notice: Subject to any disclaimer, the term of this patent is extended or adjusted under 35 U.S.C. 154(b) by 760 days.

(21) Appl. No.: 10/669,359

(22) Filed: Sep. 25, 2003

(65) Prior Publication Data
US 2005/0101823 A1    May 12, 2005

(30) Foreign Application Priority Data
Sep. 27, 2002    (EP)    ................... 02079066

(51) Int. Cl.
*A61N 5/00*    (2006.01)
(52) U.S. Cl. ......................................................... 600/3
(58) Field of Classification Search .................. 600/1–8
See application file for complete search history.

(56) References Cited

U.S. PATENT DOCUMENTS

| | | | | |
|---|---|---|---|---|
| 3,872,856 A | | 3/1975 | Clayton | |
| 5,653,683 A | * | 8/1997 | D'Andrea | .................... 604/21 |
| 5,863,285 A | * | 1/1999 | Coletti | ........................... 600/3 |
| 5,913,813 A | * | 6/1999 | Williams et al. | ............... 600/3 |
| 5,938,582 A | | 8/1999 | Ciamacco et al. | |
| 6,409,652 B1 | * | 6/2002 | Kamdar et al. | ................. 600/3 |
| 6,413,204 B1 | | 7/2002 | Winkler et al. | |
| 6,482,142 B1 | * | 11/2002 | Winkler et al. | ................. 600/3 |

FOREIGN PATENT DOCUMENTS

| | | |
|---|---|---|
| EP | 0 719 571 A2 | 7/1996 |
| WO | WO 98/01183 A1 | 1/1998 |

\* cited by examiner

*Primary Examiner*—Samuel G Gilbert
(74) *Attorney, Agent, or Firm*—Birch, Stewart, Kolasch & Birch, LLP

(57) ABSTRACT

A device for radiation treatment of proliferative tissue surrounding a cavity in an animal body includes at least a first inflatable chamber having a wall for placement in the cavity, a supportive probe having an elongated body with a distal end connected with the first inflatable chamber and a proximal end remaining outside the cavity, a device for inflating and deflating the first chamber, and a radiation delivering device for placing at least one energy emitting source within the cavity for performing said radiation treatment. It is possible to temporarily position a solid energy emitting source in a reproducible manner at different locations within the inflated chamber, such that subsequent identical radiation treatment sessions can be performed, whereas the comfort of the patient is maxim and an out hospitalization treatment is possible.

14 Claims, 6 Drawing Sheets

Figures 1A, 1B:
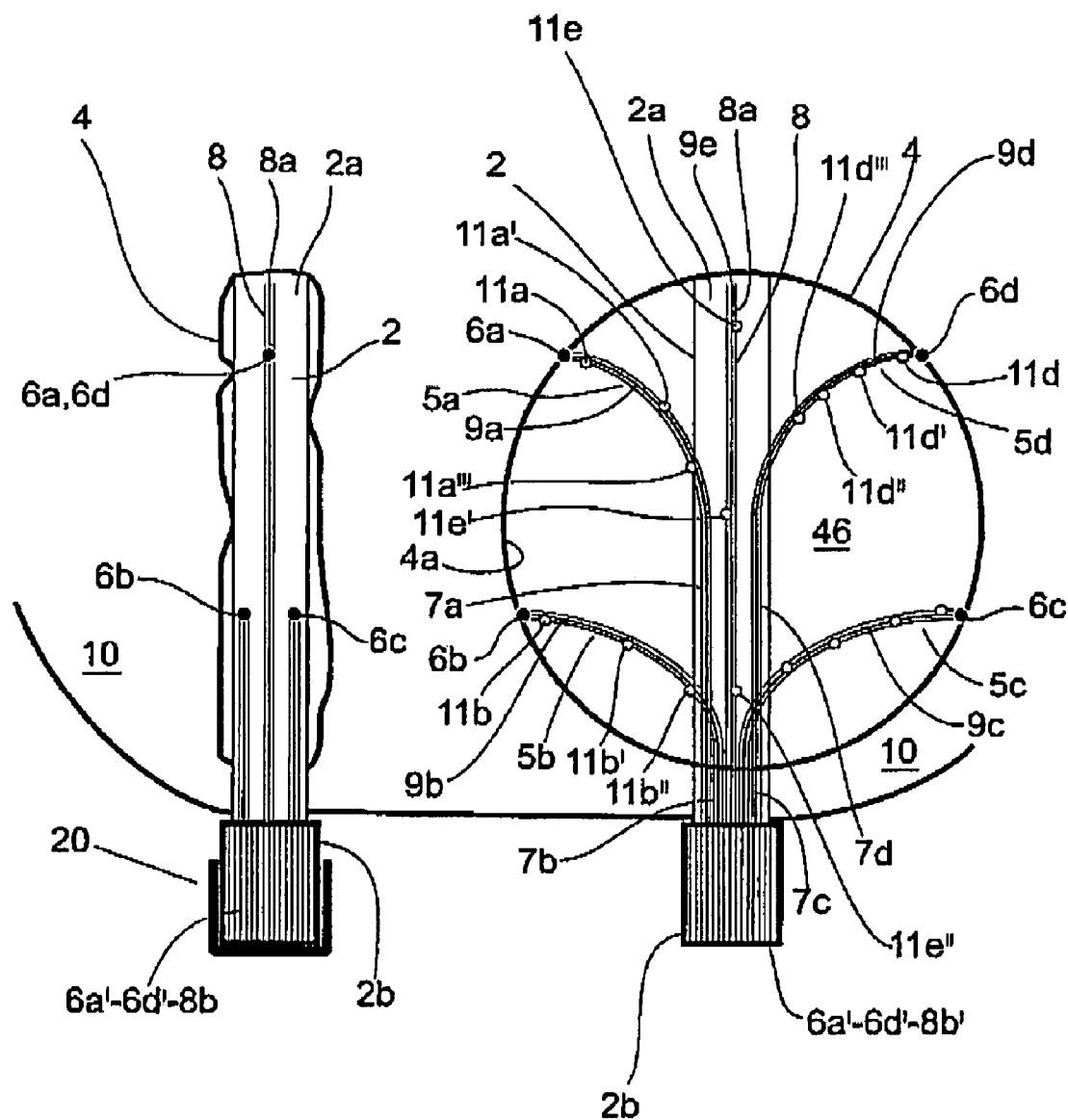

DEVICE FOR RADIATION TREATMENT OF PROLIFERATIVE TISSUE SURROUNDING A CAVITY IN AN ANIMAL BODY

This nonprovisional application claims priority under 35 U.S.C. § 119(a) on Patent Application No(s). 02079066.3 filed in European Patent Office on Sep. 27, 2002, which is(are) herein incorporated by reference.

The invention relates to a device for radiation treatment of proliferative tissue surrounding a cavity in an animal body comprising:

at least a first inflatable chamber having a wall for placement in said cavity;

a supportive probe having an elongated body with a distal end connected with said at least first inflatable chamber and a proximal end remaining outside said cavity;

inflation means for inflating and deflating said at least first chamber;

radiation delivering means for placing at least one energy emitting source within said cavity for performing said radiation treatment.

Such a device is for example known from the U.S. Pat. No. 5,492,582. In U.S. Pat. No. 5,492,582 a method and apparatus are described for treating tissue surrounding a surgically excised tumour with radioactive emissions to kill any cancer cells that may be present in the margins surrounding the excised tumour. Following surgical removal of a tumour, say in the brain or breast, a supportive probe having an inflatable chamber connected at a distal end thereof is introduced into the removal of a tumour. Subsequently the deflated chamber is inflated by suitable inflation means by injecting a fluid having radionuclide(s) therein within the distensible reservoir formed by the chamber, via a passageway in the supportive probe.

When it is considered that the absorbed dose rate at a point exterior to the radioactive source is inversely proportional to the square of the distance between the radiation source and the target point, tissue directly adjacent the wall of the inflated chamber may be exposed to an excessive amount of radiation, which "hot spots" may result in healthy tissue necrosis. In general, the amount of radiation desired by the physician is a certain minimum amount, that is delivered to a position 0-3 cms away from the wall of the excised tumour. It is desirable to keep the radiation in the space between that position and the wall of the inflated chamber as uniform as possible to prevent over-exposure to tissue at or near the reservoir wall. In treating other cancers, such as bladder cancer, where the neoplastic tissue is generally located on the bladder surface, deep penetration is unnecessary and to be avoided.

In U.S. Pat. No. 5,913,813 and U.S. Pat. No. 6,413,204 a suppportive probe is described also provided with an inflatable chamber connected to the distal end thereof. The inflatable chamber comprises an inner wall and an outer wall, resulting in—when inflated—a chamber with an inner spatial volume and an outer spatial volume surrounding the first spatial volume.

Similar to U.S. Pat. No. 5,429,582 the first spatial volume can be inflated using a liquid or solution containing radionuclide(s) by suitable inflation means via a suitable passageway present in the supportive probe. Hence the device according to U.S. Pat. No. 5,913,813 comprises two spherical chambers, one inside the other and appropriately spaced apart from each other.

However, the spacing between the inner and outer chambers needs to be held constant to avoid "hot spots" in the emitted radiation dose profile. This result can be achieved by careful placement of precision blown polymer parisons or by using compressible foams or mechanical spacers in the form of webs joining the inner wall to the outer wall, making the overall construction of U.S. Pat. No. 5,913,813 more complicated and costly.

Therefore a need exists for a device, which may be used to deliver radiation from at least one energy emitting source to a target tissue within a cavity inside the animal body with a conformal radiation dose profile and of a desired intensity and at a predetermined distance from the radiation source without over-exposure of body tissue disposed between the radiation source and the target.

Furthermore the invention aims to provide a device according the above preamble, wherein it is possible to temporarily position a solid energy emitting source in a reproducible manner at different locations within the inflated chamber, such that subsequent identical radiation treatment sessions- can be performed, whereas that the comfort of the patient is maxim and an out hospitalization treatment is possible.

According to the invention said radiation delivering means comprises at least one hollow, flexible tunnel channel having at least one fixation point to said inner or outer wall of said first inflatable chamber and a proximal end remaining outside said cavity; and wherein said at least one hollow, flexible tunnel channel serves to guide said at least one radiation emitting source inside said cavity.

With the device according to the invention an exact positioning of one or more solid energy emitting sources within the cavity to be treated is obtained. Moreover-the positioning of the energy emitting sources can be reproduced allowing subsequent radiation treatment sessions. This allows the energy emitting source to be inserted in a reproducible manner into each tunnel channel during the subsequent radiation treatment sessions, which are therefore identical, resulting in a very precise overall radiation treatment.

More in particular said inflatable chamber is accommodated around said distal end of said supportive probe.

In a first embodiment a distal end of said at least one hollow, flexible tunnel channel is fixed to the inner side of said wall of said first inflatable chamber. In an advantageous embodiment said at least one tunnel channel is accommodated in a corresponding longitudinal groove present in the circumferential surface of said elongated body of said supportive probe, when said chamber is deflated.

In order to perform a spatial radiation treatment session exposing the tissue in the cavity with an accurate and precise radiation dose distribution the supportive probe according to the invention is provided with a plurality of longitudinal grooves present in said circumferential surface for accommodating a corresponding plurality of tunnel channels. This allows a proper storage and orientation of the tunnel channels during transport and insertion into a cavity without the risk of damage.

In order to obtain a precise radiation distribution the distal ends of said plurality of flexible tunnel channels are arranged in at least one perpendicular plan relative to the supportive probe. By using this approach, a conformal distribution is obtained.

In a second embodiment of the device according to the invention said at least one hollow, flexible tunnel channel is fixed to the outer side of said wall of said first inflatable chamber. More in particularly a plurality of said tunnel channels are fixed equidistant on the outer side of the wall of the first inflatable chamber. This also ensures a specific, well determined radiation dose distribution and avoids an over-exposure of healthy tissue to radiation.

To avoid hot spots at the contact surface with the tissue in a further embodiment said first inflatable chamber is surrounded by a second inflatable chamber, wherein said first and second inflatable chambers are separated by a third inflatable chamber system placed equidistant between said tunnel channels.

In a further embodiment said radiation delivering means comprises further at least one central catheter bore having a proximal remaining outside said cavity and distal end extending in longitudinal direction within said elongated body of said supportive probe.

Another advantageous embodiment of the device is characterized in that it further comprises protection means for covering said proximal end of said hollow tunnels, when the patient is not treated. As the inflated chamber inside a cavity, for example inside the head or a breast (of a woman) positions the tunnel channels in a fixed manner inside the cavity relative to the target tissue to be treated, this allows to place and inflate the chamber, the energy emitting source can be inserted in a reproducible manner through insertion catheters into each tunnel channel, during the subsequent radiation treatment sessions, which are therefore identical, resulting in a very precise overall radiation treatment.

After each individual radiation treatment session the energy emitting source are retracted from the insertion catheter present in each tunnel channel, which insertion catheters are subsequently retracted and the proximal ends of the tunnel channels are then covered and protected with the cap. The device according to the invention has a part placed outside the cavity with minimized dimensions increasing the patient's comfort. This part can be covered by a protection cap in between subsequent radiation treatment sessions and thus the patient is allowed to move freely with a minimum of discomfort, he/she may even leave the hospital with the inflated chamber stay fixed inside the cavity and the cap is removed when a next-treatment session has to performed.

For guiding said at least one energy emitting source through said at least one tunnel channel until within said cavity at least one hollow insertion catheter with a proximal end and a distal end is introduced into said at least one tunnel channel.

More in particular said at least one hollow insertion catheter is connected with it's proximal end to an afterloader device, wherein said at least one energy emitting source is contained in said afterloader device and guided through said hollow insertion catheter toward said cavity using a source wire having a distal end connected to said energy emitting source.

This allows radiation treatment sessions to be performed with High Dose Rate (HDR) or Pulse Dose Rate (PDR) energy emitting sources, which require a special and safe handling prior to each treatment session. These HDR or PDR sources are for safety reasons stored in a radiation shielded compartment within the afterloader. After the hollow insertion catheters are inserted into each tunnel channel the medical personnel leaves the treatment room and the HDR or PDR energy emitting sources are moved from said shielded compartment through said insertion catheter towards the intended treatment position in the cavity using the source wires. After the radiation treatment session each energy emitting source is safely retracted from the cavity towards the shielded compartment for storing purposes using the source wire.

This is called "remote afterloading" as the energy emitting source is "loaded" or placed at the intended treatment site after the medical personnel has left the treatment room.

The device according to the invention is suitable for incorporating different energy emitting sources, for example a High Dose Rate Ir-192 source, a Pulse Dose Rate Ir-192 source, a miniature X-ray source or a radio-waves emitting source. However the invention is not limited to the use of one of the energy emitting sources listed above.

Figure 2:
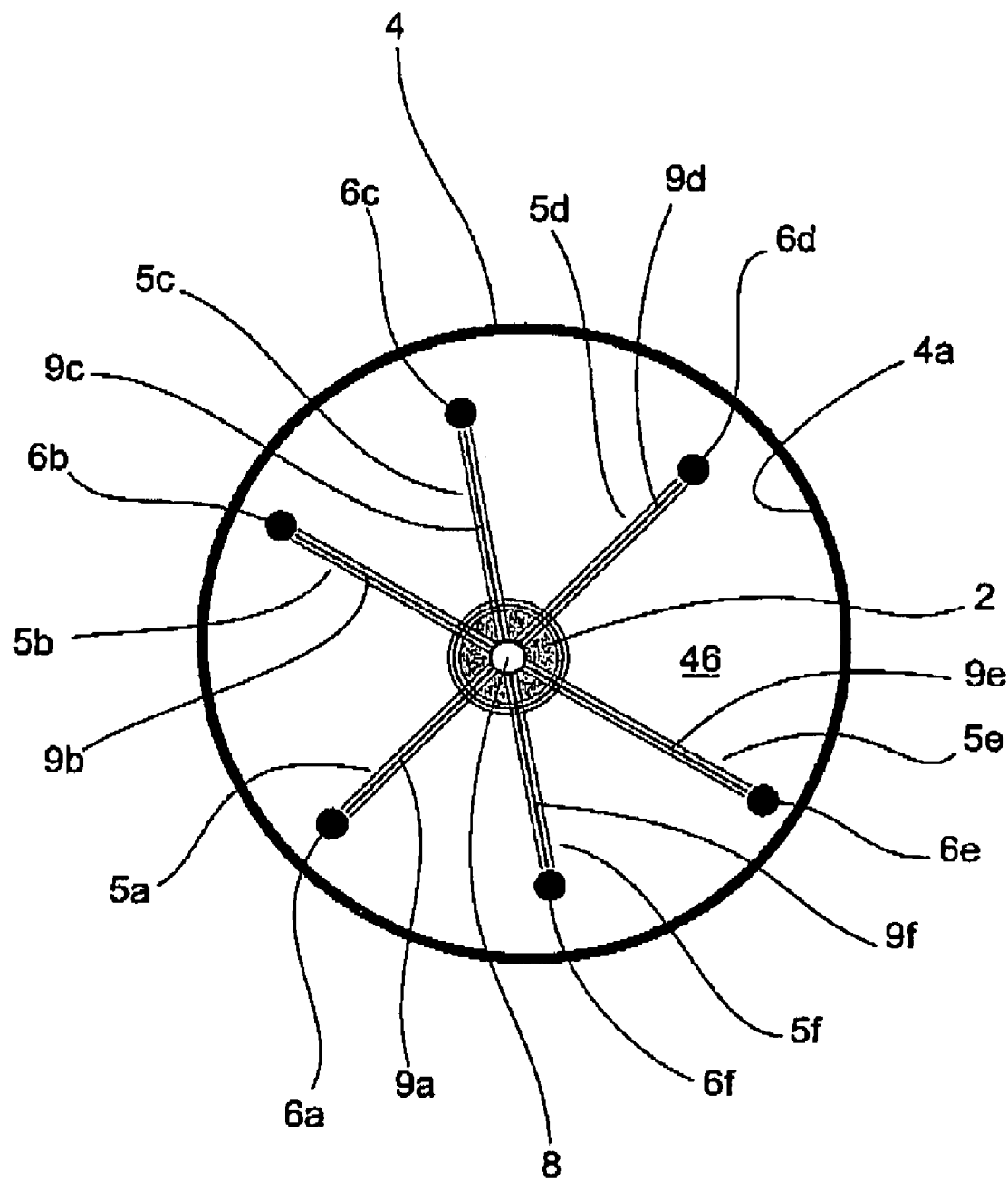
Figure 3:
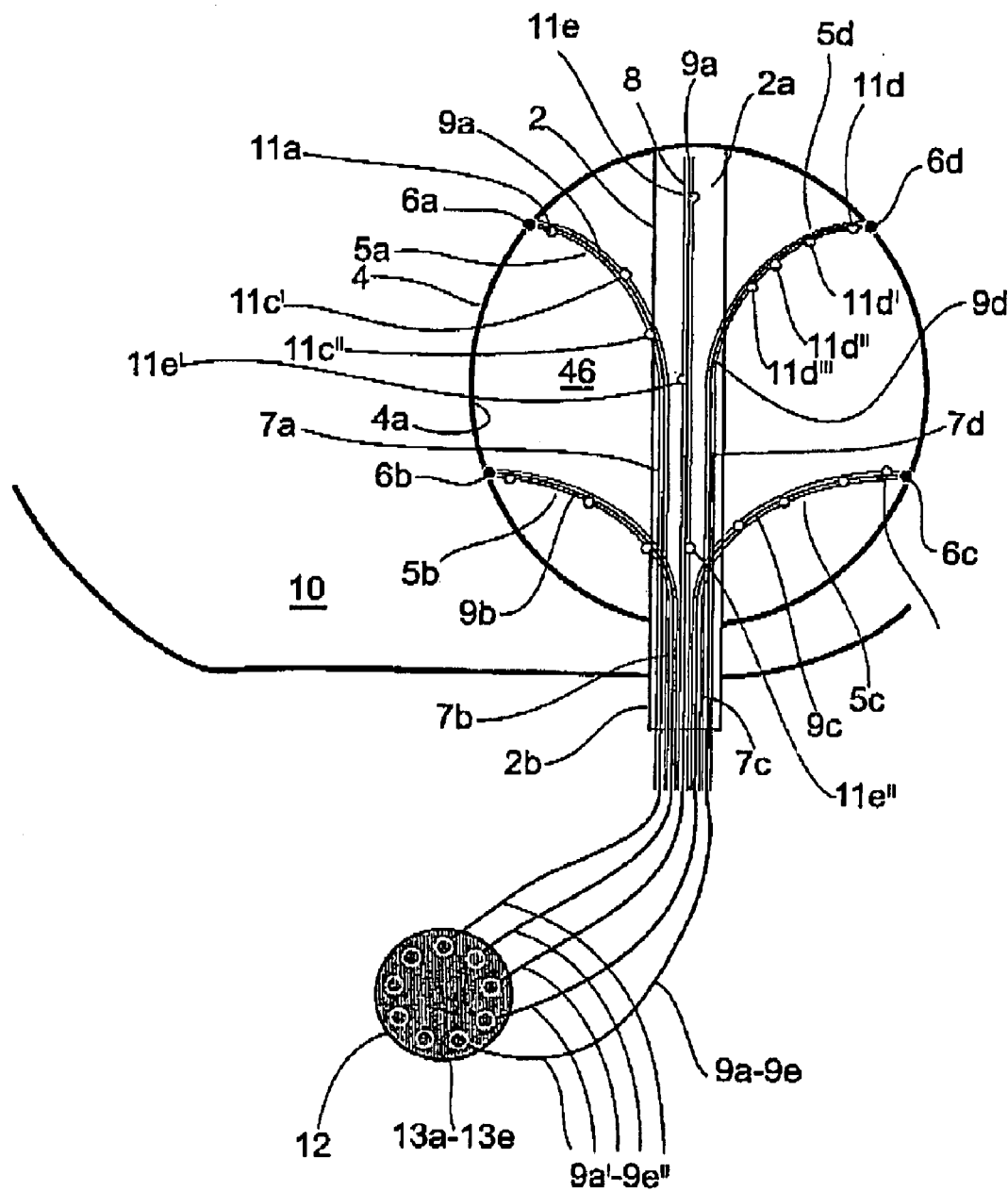
Figure 4:
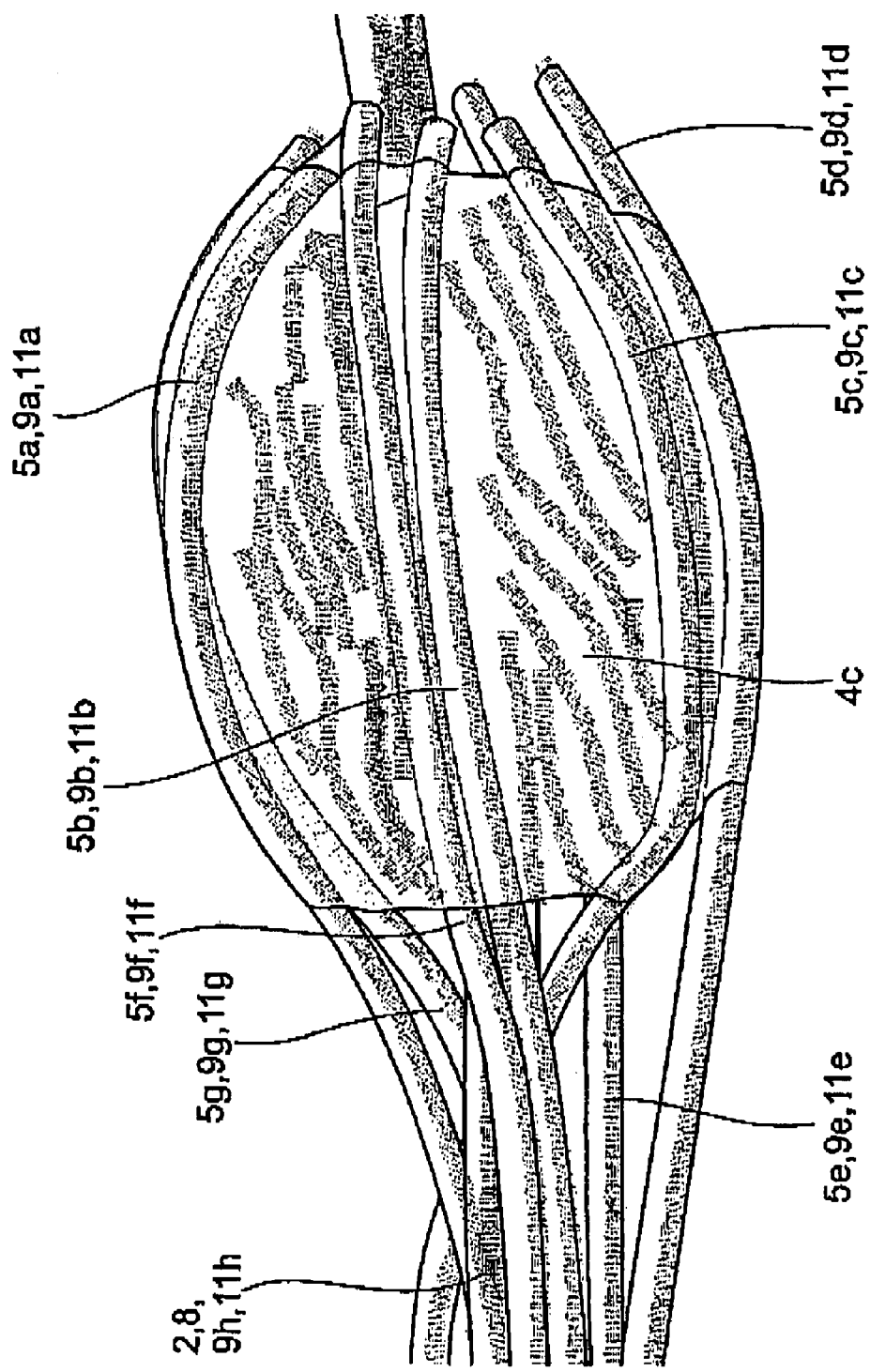
Figure 5:
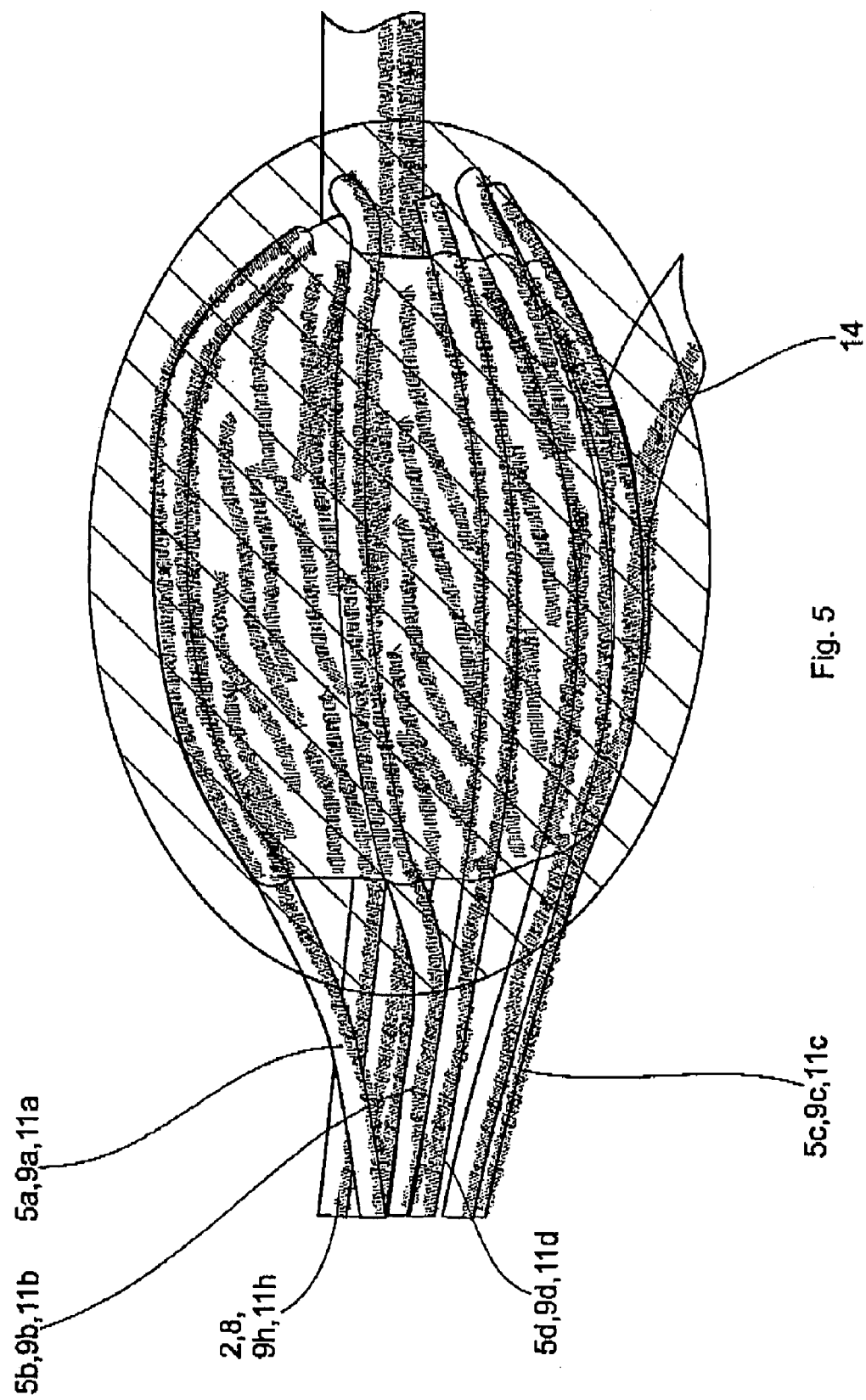
Figure 6:
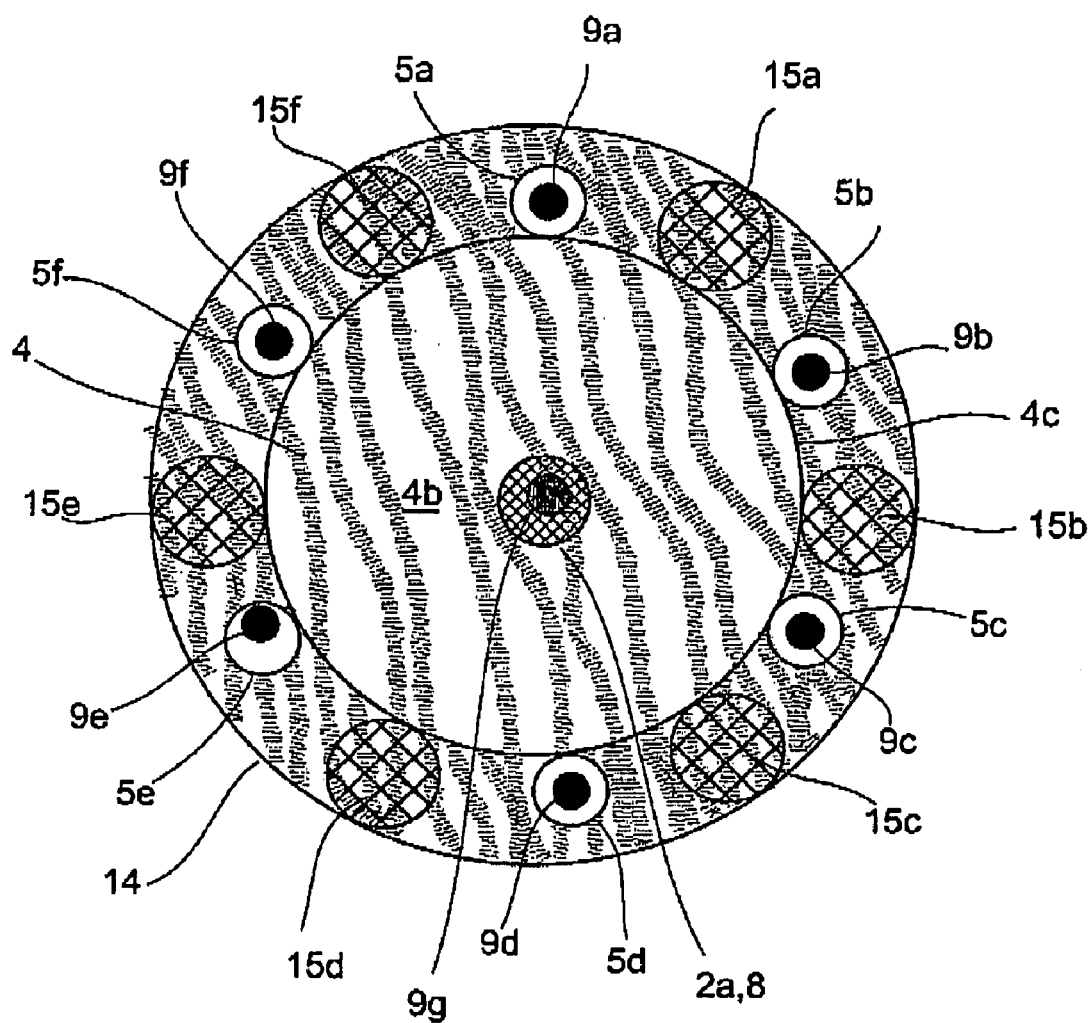

The invention will be now described with reference to the accompanying drawings, which drawings show:

FIG. 1a a lateral view of a first embodiment of a device according to the invention with a deflated chamber;

FIG. 1b a lateral view of the embodiment of the device of FIG. 1a with an inflated chamber;

FIG. 2 a upper view of the embodiment of the device of FIG. 1b;

FIG. 3 another embodiment of a device according to the invention connected to an afterloading device;

FIG. 4 a second embodiment of a device according to the invention;

FIG. 5 a third embodiment of a device according to the invention;

FIG. 6 a sectional view of the embodiment of FIG. 5.

FIG. 1a discloses a lateral view of a first embodiment a device for radiation treatment of proliferatife tissue surrounding a cavity in an animal body according to the invention, which device 1 comprises a suppportive probe 2 having a distal end 2a and a proximal end 2b. The supportive probe 2 consists of an elongated body, denoted with the same reference number 2, which is enveloped by an inflatable chamber 3, e.g. a balloon. The device 1 is used to be implanted inside a cavity 10 within an animal body, which cavity is created due to the surgical removal of a tumour, for example a cancer tumour in the brain or the breast (of a woman) of a patient. The device 1 is so constructed, that only the distal end 2a of the elongated body of the supportive probe 2 together with the inflatable chamber 3 enveloping said distal end 2a are present inside said cavity 10, whilst the proximal end 2b of the elongated body of the supportive probe 2 remains outside the cavity 10 and preferably outside the animal body.

The device according to the invention is used for treating tissue surrounding a surgically excised tumour with radiation emissions to kill cancel cells that may be present in the margin surrounding the excised tumour. For this purpose after insertion of the supportive probe 2 and the inflated chamber 3 surrounding the supportive probe the deflated chamber 3 is inflated using suitable inflation means (not shown) which are preferably connected with the proximal end 2b of the supportive probe 2 outside the cavity of the animal body.

This situation is shown in FIG. 1b showing the lateral view of the device 1 of FIG. 1a, now in inflated state.

As stated and explained above the invention claims to provide a device having a supportive probe and an inflatable chamber for insertion into a cavity in an animal body, wherein it is possible to temporarily position a solid energy emitting source in a reproducible manner at different locations within the inflated chamber. With this aim subsequent identical radiation treatment sessions can be performed, whereas the comfort of the patient is maxim and an out hospitalisation treatment is possible.

As shown in the lateral view of FIG. 1b showing the device according to the invention in inflated state, several hollow tunnel channels 5a-5d are present within the inflated chamber, which hollow tunnel channels 5a-5d are connected with their distal ends 6a-6d at certain predetermined positions with the inner wall 4a of the inflated chamber 4, such that—as shown in FIG. 1a—the hollow tunnel channels 5a-5d are orientated within the spherical chamber 4d created by the inflated chamber 4. As the position of the distal ends 6a-6d of the hollow tunnel channels 5a-5d are predetermined also the orientation of the hollow tunnel channels 5a-5d within the spherical chamber 4b of the inflated chamber 4 is predetermined.

Furthermore the elongated body 2 is provided with a central passageway 8 with a distal end 8a and a proximal end 8b, which fulfills the same function as the tunnel channels 5a-5d.

Whereas the distal ends 6a-6d of the hollow tunnel channels 5a-5d are fixed at the inner wall 4a of the inflated chamber 4, the proximal ends 6a'-6d' of the hollow tunnel channels 5a-5d and the proximal end 8b of the central tunnel channel 8 are present at the proximal end 2b of the supportive probe 2 remaining outside the cavity 10 of the animal body.

For a proper storage of the hollow tunnel channels 5a-5d in the deflated states and to prevent damage to the hollow tunnel channels during insertion of the device 1 according to the invention in a cavity 10 inside an animal body, the elongated body of the supportive probe 2 is provided with longitudinal groves present 7a-7d in the circumferential service 3 of the elongated body 2, which grooves 7a-7d serve to accommodate and store each tunnel channel 5a-5d.

Although in the embodiments shown in the FIGS. 1a-1b only four hollow tunnel channels 5a-5d are disclosed connected with their respective distal end 6a-6d with the inner wall 4a of the inflatable chamber 4 it will be evident that also less or more hollow tunnel channels can be used in this invention.

The hollow tunnel channels 5a-5d-8 serve to guide a solid energy emitting source through the hollow tunnel channel 5a-5d-8 to a certain position within said tunnel channel and the inflatable chamber 4. More in particular, for applying a solid energy emitting source 11a-11e towards a position within the cavity 10 so-called hollow insertion catheters 9a-9e are inserted in each hollow tunnel channel 5a-5d-8. Subsequently, following the positioning of the insertion catheters 9a-9e in each hollow tunnel channel 5a-5d-8 solid energy emitting sources are inserted into each catheter 9a-9e and guided through the catheter 9a-9e (and thus through the hollow tunnel channel 5a-5d-8) towards a postion within the cavity 10.

In the drawings the hollow insertion catheters in the respective hollow tunnel channels 5a-5d-8 are depicted with the reference numerals 9a-9e, whereas the solid energy emitting sources within the hollow insertion catheters 9a-9e are depicted with the reference numerals 11a-11e. Furthermore the reference numerals, 11a-11a'-11a" respectively (or 11d-11d'-11d"-11d''') in FIG. 3 represents different positions of the energy emitting sources 11a-11d-11e respectively within the hollow tunnel channel 5a-5d-8 respectively. The positioning of the solid energy emitting sources 11a-11d-11e at different locations within their respective insertion catheter 9a-9e in each hollow tunnel channel 5a-5d-8 gives more possibilities for performing a radiation therapy treatment session. The total dose distribution of the tissue to be treated will be conformal with the volume of tumor tissue by optimizing the dwell times for the different positions 11a-11' of the solid-energy emitting source.

In the device according to the invention, by inserting a solid energy emitting source through the insertion catheters 9a-9e present in the tunnel channels 5a-5d-8 towards a certain, predetermined position within the cavity 10. Moreover the guidance of the solid energy emitting sources through a hollow insertion catheter 9a-9e within the hollow tunnel channels 5a-5d allows a temporarily insertion of the source in a reproducible manner at different locations.

The latter allows that subsequent identical radiation treatment sessions can be performed, significantly improving the quality of the radiation therapy treatment and the result achieved.

An example of a radiation treatment is now described in combination with FIG. 3, whereby an afterloader device (schematically depicted with reference number 12) is used for performing radiation therapy treatments of the tissue surrounding the cavity 10.

With the use of an afterloader device 12 it is possible to use the device according to the invention to perform radiation therapy treatment sessions with so called High Dose Rate (HDR) or Pulse Dose Rate (PDR) energy emitting sources, which require a special and safe handling prior to each treatment session. These HDR or PDR sources are characterized by a high radiation intensity profile and are thus for safety reasons stored in a radiation shielded compartment within the afterloader 12. Performing radiation therapy treatment sessions with such high intensity energy emitting sources requires specific proceedings concerning handling and storage of these sources.

For performing radiation therapy treatments with the device according to the invention using HDR or PDR sources (or other energy emitting sources having a high radiation intensity) hollow insertion catheters 9a-9d-9e are inserted into each hollow tunnel channel 5a-5d-8 with their respective distal ends. Said hollow insertion catheters 9a-9d-9e extend outside the proximal ends 6a'-6d'-8b of said hollow tunnel channels 5a-5d-8. More in particularly they are connected with their proximal ends 9a"-9e" with suitable source openings 13a-13e present in the housing of the afterloader device 12.

Subsequently the energy emitting source can be redirected through an other insertion catheter (for example 9d) through the tunnel channel 5d towards a position within the inflated chamber (for example position 11d').

Likewise a corresponding insertion catheter 9e can be used for inserting an energy emitting source 11e through the central bore 8.

When using an afterloader device subsequent radiation therapy treatments can be performed by using one energy emitting source or by inserting several emitting sources simultaneously at the same or a different location within, each hollow tunnel channel 5a-5d and 8 through the insertion catheters 9a-9e.

The use of an afterloader device 12 connected with several insertion catheters 9a-9e inserted in the several hollow tunnel channels 5a-5d-8 and the subsequent insertion of one or more solid energy emitting sources through said hollow insertion catheters 9a-9e using a source wire driven by suitable source driver means ensures the positioning of each energy emitting source in a fixed position within each tunnel channel 5a-5d and 8 or the guidance of each energy emitting source in a stepwise manner within each tunnel channel (insertion catheters) towards a plurality of positions within each insertion catheter (and tunnel channel).

This allows a number of different radiation therapy treatments sessions to be performed, depending on the individual case of the patient.

The use of an afterloader device 12 with the device according to the invention makes it possible to perform subsequent radiation treatments sessions during a longer period of times (days or weeks) as the device according to the invention allows a temporarily but accurate placement of the energy emitting source in a reproducible manner for subsequent identical radiation treatment sessions.

For that purpose the supportive probe 2 with the inflated chamber 4 remains within the cavity of the patient for that prolonged period of time allowing the patient to move freely, even outside the hospital and discomforts the patient to a minimum.

For each subsequent radiation treatment session the patient returns to the hospital where he/she is coupled to the afterloader device 12 for conducting a subsequent radiation treatment session. In between subsequent radiation treatment sessions a protection cap (not shown) can be placed over the proximal end 2b of the supportive probe 2 and the proximal ends 6a'-6d' and 8b.

The inflating means for inflating and deflating the chamber 4 through a suitable passageway present within the supportive probe 2 and ending inside the chamber 4 (not shown) are provided with a valve or other suitable closure means.

In FIG. 2 a frontal or upper view of the inflated chamber 4 of the device according to the invention is shown. The distal ends 6a-6f of, in this embodiment six, tunnel channels 5a-5f are connected to the inner wall 4a of the chamber 4 in such manner, that they are arranged in at least one perpendicular plane relative to the supportive probe 2. Due to this geometrical orientation the placement of energy emitting sources within each tunnel channel will result in a radiation therapy treatment session with a uniform radiation dose distribution and exposure of the tissue. The radiation dose distribution obtained in this way will follow outside the chamber the conformal specification of the radiation dose in the surrounded tissue of the chamber.

In FIG. 4 another embodiment of the device for radiation treatment of proliferative tissue surrounding a cavity in an animal body is disclosed.

Parts of the embodiment of FIG. 4 corresponding with parts disclosed in FIGS. 1-3 are denoted with identical reference numerals.

The embodiment of FIG. 4 comprises a supportive probe 2 on which an inflatable chamber 4 or balloon is mounted. The inflatable chamber 4 can be inflated and deflated by suitable (not shown) inflation means once inserted into a cavity in an animal body.

A plurality of tunnel channels 5a-5g are fixed to the outer wall 4c of the inflatable chamber or balloon 4. The tunnel channels 5a-5g extend in longitudinal direction of the supportive probe 2 and are in a specific embodiment (shown in FIG. 4) fixed in an equidistant manner on the outer side of the wall 4c.

Similar to the embodiment shown in FIG. 1a-1b, 2 and 3 this construction ensures a precise radiation dose distribution during subsequent radiation treatment sessions, whereas the solid energy emitting sources (not shown), which are to be inserted through the insertion catheters present in each tunnel channel within the cavity, can be accurately positioned.

The plurality of hollow tunnel channels 5a-5g which are fixed to the outer wall 4c of the inflated chamber 4 serve to guide hollow insertion catheters 9a-9g, which are inserted from the proximal end of the supportive probe extending outside the cavity of the animal body towards the cavity 10 in which the inflated chamber 4 is positioned.

In a similar manner like the embodiments described with reference to the FIGS. 1a-1b, 2 and 3, through each hollow insertion catheter 9a-9g solid energy emitting sources 11a-11g are inserted using a source wire (not shown) having a distal end connected with said energy emitting source.

Likewise the supportive probe 2 can be provided with a central bore 8 through which a corresponding insertion catheter 9h can be placed for inserting an energy emitting source 11h within the inflated chamber 4.

As an additional protection of the tunnel channels 5a-5g placed on the outer side of the wall 4c of the inflated chamber 4 a second inflatable chamber 14 can be placed surrounding the first inflatable chamber 4 as well as the plurality of tunnel channels 5a-5g. This embodiment is disclosed in FIG. 5 whereas FIG. 6 discloses a sectional view of this embodiment. Also in this two FIGS. 5-6 identical parts are denoted with identical reference numbers.

In order to ensure a proper orientation of the tunnel channels 5a-5f and thus the energy emitting sources 11a-11f to be positioned within the insertion catheters 9a-9f placed within these tunnel channels 5a-5f said first and second inflatable chambers 4 and 14 are separated by a third inflatable chamber system 15 comprising of a plurality of inflatable chambers 15a-15f. These plurality of third inflatable chambers 15a-15f are placed equidistant between the flexible tunnel chambers 5a-5f, thus ensuring a fixed positioning within the cavity 10 at the time the first and second inflatable chambers 4 and 14 are placed inside a cavity and subsequently inflated by the inflation means. Likewise through the plurality of tunnel channels 5a-5f hollow insertion catheters 9a-9f are inserted for placing an energy emitting source 11a-11f using a source wire connected to an afterloader device.

Also with this embodiment disclosed in FIGS. 5 and 6 a precise dose distribution can be obtained when performing subsequent radiation treatment sessions.

The invention claimed is:

1. Device for radiation treatment of proliferative tissue surrounding a cavity in an animal body comprising:
    at least a first inflatable chamber having a wall for placement in said cavity;
    a supportive probe having an elongated body with a distal end connected with said at least first inflatable chamber and a proximal end remaining outside said cavity;
    inflation means for inflating and deflating said at least first chamber;
    radiation delivering means for placing at least one energy emitting source within said cavity for performing said radiation treatment, wherein
    said radiation delivering means comprises at least one hollow, flexible tunnel channel having at least one fixation point to said wall of said first inflatable chamber and a proximal end remaining outside said cavity;
    said at least one hollow, flexible tunnel channel serves to guide said at least one radiation emitting source inside said cavity, wherein a distal end of said at least one hollow, flexible tunnel channel is fixed to the inner side of said wall of said first inflatable chamber and when said chamber is deflated said at least one tunnel channel is accommodated in a corresponding longitudinal groove present in the circumferential surface of said elongated body of said supportive probe.

2. Device according to claim 1, wherein said first inflatable chamber is accommodated around said distal end of said supportive probe.

3. Device according to claim 1, wherein said supportive probe is provided with a plurality of longitudinal grooves present in said circumferential surface for accommodating a corresponding plurality of tunnel channels.

4. Device according to claim 3, wherein said digital ends of said plurality of tunnel channels are arranged in at least one perpendicular plan relative to the supportive probe.

5. Device according to claim 1, wherein said radiation delivering means further comprise at least one central catheter bore having a proximal end remaining outside said cavity and a distal end extending in longitudinal direction within said elongated body of said supportive probe.

6. Device according to claim 1, wherein the device further comprises protection means for covering said proximal end of said supportive probe, said proximal end of said at least one tunnel channel and said proximal end of said at least one central catheter bore, when the patient is not treated.

7. Device according to claim 1, wherein for guiding said at least one energy emitting source through said at least one tunnel channel until within said cavity at least one hollow insertion catheter with a proximal end and a distal end is introduced into said at least one tunnel channel.

8. Device according to claim 7, wherein said at least one hollow insertion catheter is connected with its proximal end to an afterloader device.

9. Device according to claim 8, wherein said at least one energy emitting source is contained in said afterloader device and guided through said insertion catheter toward said cavity using a source wire having a distal end connected to said energy emitting source.

10. Device according claim to claim 1, wherein the energy emitting source is a High Dose Rate Ir-192 source.

11. Device according claim to claim 1, wherein the energy emitting source is a Pulse Dose Rate Ir-192 source.

12. Device according to claim 1, wherein the energy emitting source is a miniature X-ray source.

13. Device according to claim 1, wherein the energy emitting source is a radio-waves emitting source.

14. Device according claim to claim 1, wherein the dose distribution generated with said plurality of energy emitting sources positioned in said plurality of hollow tunnel channels will follow outside the chamber wall the conformal specification of the dose in the surrounded tissue of the first inflatable chamber.

\* \* \* \* \*